United States Patent [19]

Chenoweth

[11] Patent Number: 4,949,716
[45] Date of Patent: Aug. 21, 1990

[54] NASAL INTUBATION ADJUNCT

[75] Inventor: David Chenoweth, Lakewood, Colo.

[73] Assignee: Medical Devices, Inc., Lakewood, Colo.

[21] Appl. No.: 442,998

[22] Filed: Nov. 28, 1989

Related U.S. Application Data

[63] Continuation of Ser. No. 265,213, Oct. 31, 1988, abandoned.

[51] Int. Cl.$^5$ ............................................. A61M 16/00
[52] U.S. Cl. ........................... 128/207.14; 128/207.16; 128/207.18; 128/200.26
[58] Field of Search ............... 128/10, 11, 200.26, 128/207.14, 207.15, 207.16, 207.18

[56] References Cited

U.S. PATENT DOCUMENTS

| | | | |
|---|---|---|---|
| 2,463,149 | 3/1949 | Caine | 128/200.26 |
| 2,541,402 | 2/1951 | Caine | 128/200.26 |
| 3,314,431 | 4/1967 | Smith, Jr. | 128/200.26 |
| 3,730,179 | 5/1973 | Williams | 128/207.14 |
| 3,754,554 | 8/1973 | Felbarg | 128/200.26 |
| 3,802,440 | 4/1974 | Salem et al. | 128/200.26 |
| 3,815,606 | 6/1974 | Mazal | 128/207.16 |
| 3,913,568 | 10/1975 | Carpenter | 128/11 |
| 3,915,173 | 10/1975 | Brekke | 128/207.18 |
| 3,957,055 | 5/1976 | Linder et al. | 128/200.26 |
| 4,041,936 | 8/1977 | Carden | 128/207.15 |
| 4,150,676 | 4/1979 | Jackson | 128/207.18 |
| 4,185,639 | 1/1980 | Linder | 128/200.26 |
| 4,244,362 | 1/1981 | Anderson | 128/200.26 |
| 4,300,550 | 11/1981 | Gandi et al. | 128/207.18 |
| 4,593,689 | 6/1986 | White | 128/207.18 |
| 4,691,701 | 9/1987 | Williams | 128/207.14 |
| 4,727,872 | 3/1988 | Hawk | 128/207.14 |
| 4,742,819 | 5/1988 | George | 128/11 |
| 4,774,945 | 10/1988 | White et al. | 128/207.16 |
| 4,793,327 | 12/1988 | Frankel | 128/207.14 |
| 4,805,611 | 2/1989 | Hodgkins | 128/207.14 |
| 4,848,331 | 7/1989 | Northway-Meyer | 128/200.26 |

OTHER PUBLICATIONS

Model 1650 Laryngoscope Operator manual, American Optical.

Primary Examiner—Edgar S. Burr
Assistant Examiner—Aaron J. Lewis
Attorney, Agent, or Firm—James R. Young

[57] ABSTRACT

Disclosed is a hand-held medical device that attaches a wide range of nasally placed airway tubes to afford better control of said airway tubes, manipulation of said airway tubes by rotation and curvature the latter of which is provided by a soft, flexible manipulator containing a spring which is attached at its distal end by a braided wire the pulling of which will cause flexion of the manipulator and said airway tube that surrounds it. The device additionally allows for patient inspiration and expiration to pass unrestricted through the body of the device deflecting one-way valves positioned in clear tubes on the sides of the device allowing for visual confirmation of proper final placement of said airway tube. A stethoscope headset attached to the device provides an audible reference for guiding said airway tube and affords an additional reference to confirm proper final placement of said airway tube.

13 Claims, 4 Drawing Sheets

Fig.II
Fig.I2
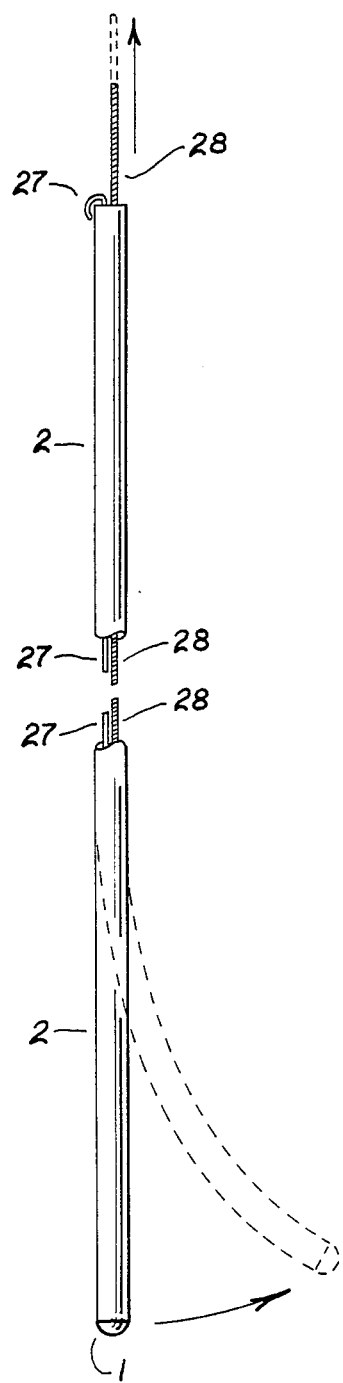
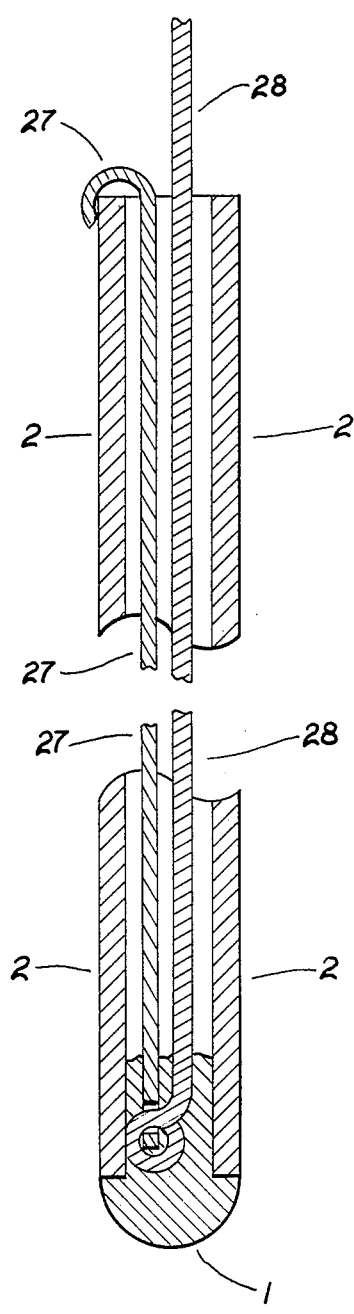

NASAL INTUBATION ADJUNCT

This application is a continuation of application Ser. No. 265,213 filed Oct. 31, 1988, now abandoned 1/12/90.

FIELD OF INVENTION

A medical device designed to improve nasal airway tube placement.

DISCUSSION OF PRIOR ART

U.S. Pat. No. 2,463,149, Mar. 1, 1949, C. W. Caine—Endotracheal Intubation Stylet—provides shaping and direction for the oral placement of endotracheal tubes but its rigid design makes it undesirable to be used in nasal endotracheal intubation.

U.S. Pat. No. 3,314,431, Apr. 18, 1967, R. M. Smith, Jr.—Stylet for insertion of endotracheal catheter—is similar in that it provides a means of manipulating the distal end of an endotracheal tube but is substantially dissimilar since it is rigid and the distal end doesn't have the ability to conform to individual variations in anatomy making it undesirable to be used in nasal endotracheal intubation.

U.S. Pat. No. 3,754,554, Aug. 28, 1973 (no name listed)—Endotracheal tube means—is a rigid device suitable only for oral intubation and not suitble for nasal endotracheal intubation.

U.S. Pat. No. 3,957,055, May 18, 1976, Gerald S. Linder—Catheter guide—is a rigid device suitable only for oral intubation and not suitable for nasal endotracheal intubation.

U.S. Pat. No. 4,185,639, Jan. 29, 1980, Gerald S. Linder—Adjustable stop for endotracheal tube guide—Similar only by providing a way to position the tip of a stylet just inside the tip of an endotracheal tube but substantially dissimilar since it fits a rigid stylet and provides no assistance in placing an endotracheal tube nasally.

The American Optical Laryngoscope Model 1650 does provide a means of guiding an endotracheal tube through a patient's glottic opening by first visually placing the end of the fiber optic flexible shaft through the nasal passage, over the hard palate and soft palate, into the posterior nasal pharynx then oral pharynx and through the glottic opening. The endotracheal tube is then slid over the flexible shaft into the patient's airway. It is substantially dissimilar since the American Optical scope can't manipulate the endotracheal tube and doesn't provide visual/audible confirmation of proper tube placement.

The "Tubestat" lighted stylet marketed by Concept Corp., Clearwater, Fla., 1-800-237-0169, provides a bright light at the end of the nasally placed endotracheal tube to help guide the tube midline. It is substantially dissimilar since it doesn't manipulate the endotracheal tube and doesn't provide audible confirmation of proper tube placement.

SUMMARY OF THE INVENTION

Accordingly several objects and advantages of my invention are: to provide a medical device giving better control of a nasally placed airway tube conforming it to the patient's anatomy thus minimizing soft tissue trauma and allowing the distal tip of said nasally placed airway tube to be more accurately placed adjacent to the patient's glottic opening, to provide a medical device with a simple means of attaching said nasally placed airway tube to allow for rapid removal of the nasal intubation adjunct from the airway tube as soon as proper placement of said nasally placed airway tube is confirmed, to provide a medical device affording confirmation of proper placement of the distal tip of said nasally placed airway tube adjacent to the patient's glottic opening, when appropriate, by increased audible sounds transmitted to the user's ears through a stethoscope headset attached to the nasal intubation adjunct, to provide a medical device that will allow adequate movement of the patient's inspired and expired air if said nasally placed airway tube is placed through the patient's glottic opening into the patient's trachea, to provide a medical device allowing confirmation of accurate placement of said nasally placed airway tube in the patient's trachea, if appropriate, by audible and visual means, to provide a medical device that will allow the user a safe working distance from the patient's face for better visualization of tube placement plus reducing the risk to the user of contamination from a diseased patient, to provide a medical device that will allow for adjustability to accommodate a wide range of said nasally placed airway tubes.

DRAWINGS

FIG. 11 shows a side view of the manipulator assembly with an indication of movement when braided wire 28 is pulled.

FIG. 12 shows an enlarged sectional side view of the manipulator.

DETAILED DESCRIPTION

Figure 1:
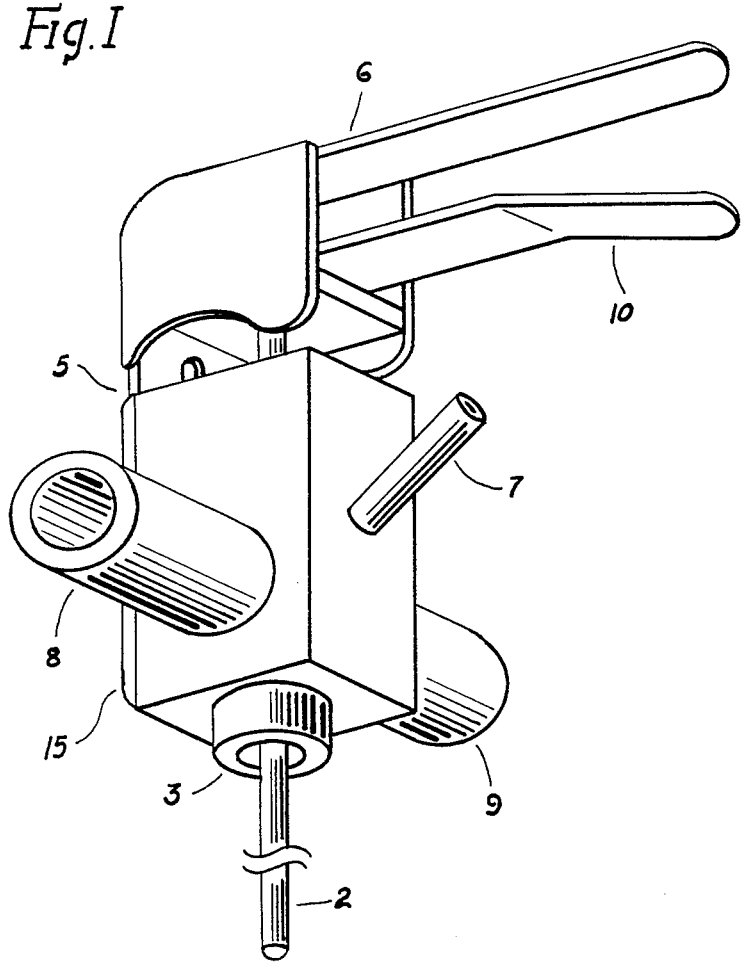
FIG. 1 shows a perspective view of the entire device.
Figure 2:
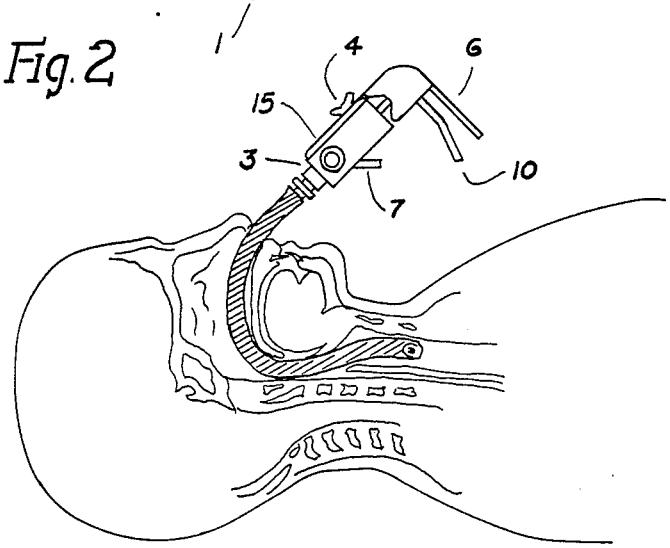
FIG. 2 shows a view of the device attached to an endotracheal tube (shaded) successfully placed nasally into patient's airway.
Figure 3:
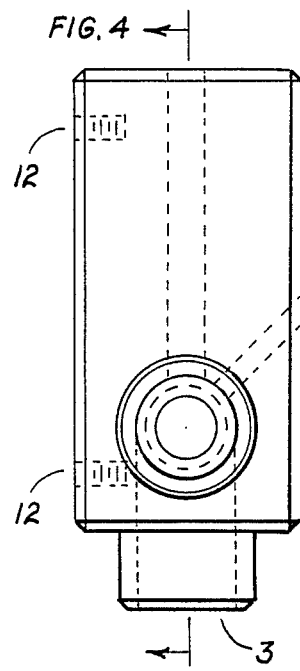
FIG. 3 shows a side view of the device's main body.
Figure 4:
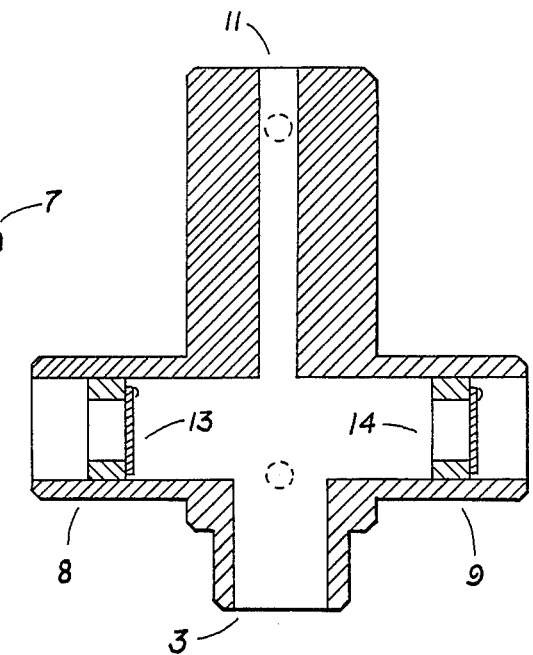
FIG. 4 shows a sectional view of the device's main body with the section indicated in FIG. 3 along the line 4—4.
Figure 5:
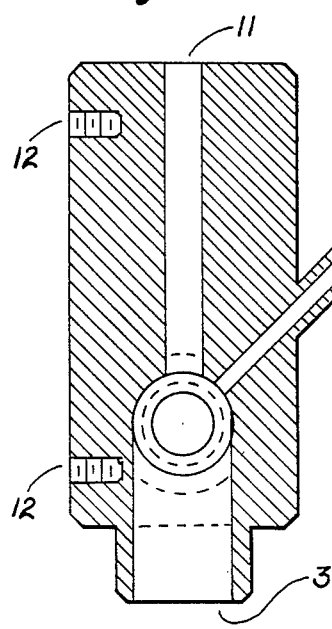
FIG. 5 shows a sectional view of the device's main body with the section indicated in FIG. 6 along the line 5—5.
Figure 6:
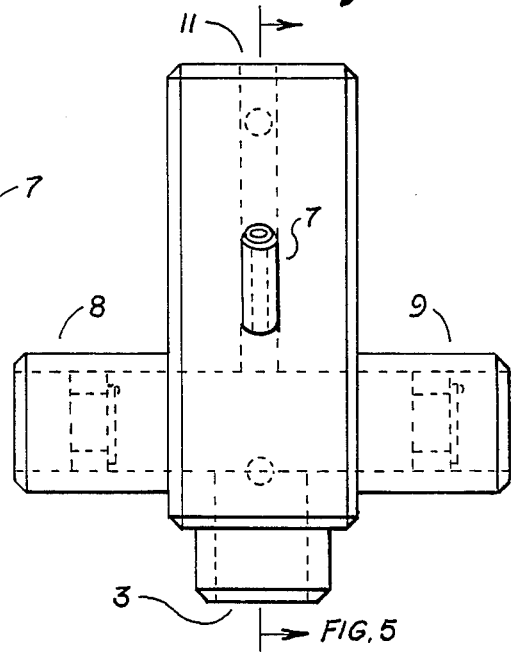
FIG. 6 shows a rear view of the device's main body.
Figure 7:
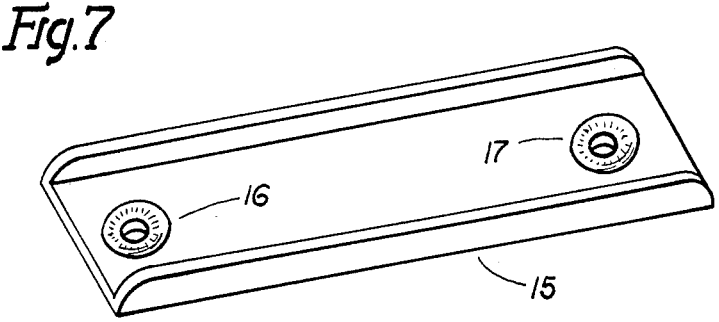
FIG. 7 shows a perspective of the slide track.

The nasal intubation adjunct consists of a body FIGS. 3, 4 5 and 6 which can be cast as a unit or constructed from its several component parts. Fitting 3 at the bottom is bored vertically with a hole 15.5 mm in diameter with said hole communicating with a hole of similar diameter bored horizontally across the device to form tubes 8 and 9 which should be transparent. Hole 11 is drilled centrally and vertically from the top slightly larger than the outside diameter of the manipulator FIG. 11 to communicate with the holes in tubes 8 and 9 and fitting 3. One-way valves 13 and 14 are placed in positions in tubes 8 and 9 to be visible looking at the sides of transparent tubes 8 and 9. One-way valve 13 should be inserted to allow air movement into tube 8 while one-way valve 14 should be inserted to allow air movement out of the device through tube 9. Port 7 is comprised of a tube of outside diameter that will accommodate the tube of a one-tube stethoscope angled at approximately 45° to the main body with a hole drilled through to communicate with the holes forming tubes 8 and 9 and the hole in fitting 3. Tapped holes 12 allow for the attachment of the slide track 15.

Figure 8:
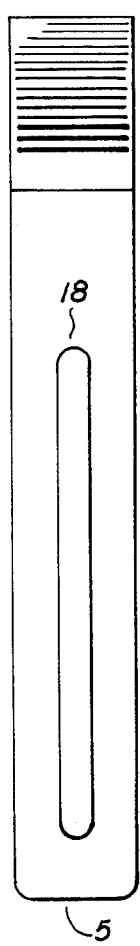
FIG. 8 shows a front view of the manipulator actuating/positioning system in FIG. 9 without hidden lines in illustrate slot 18.
Figure 9:
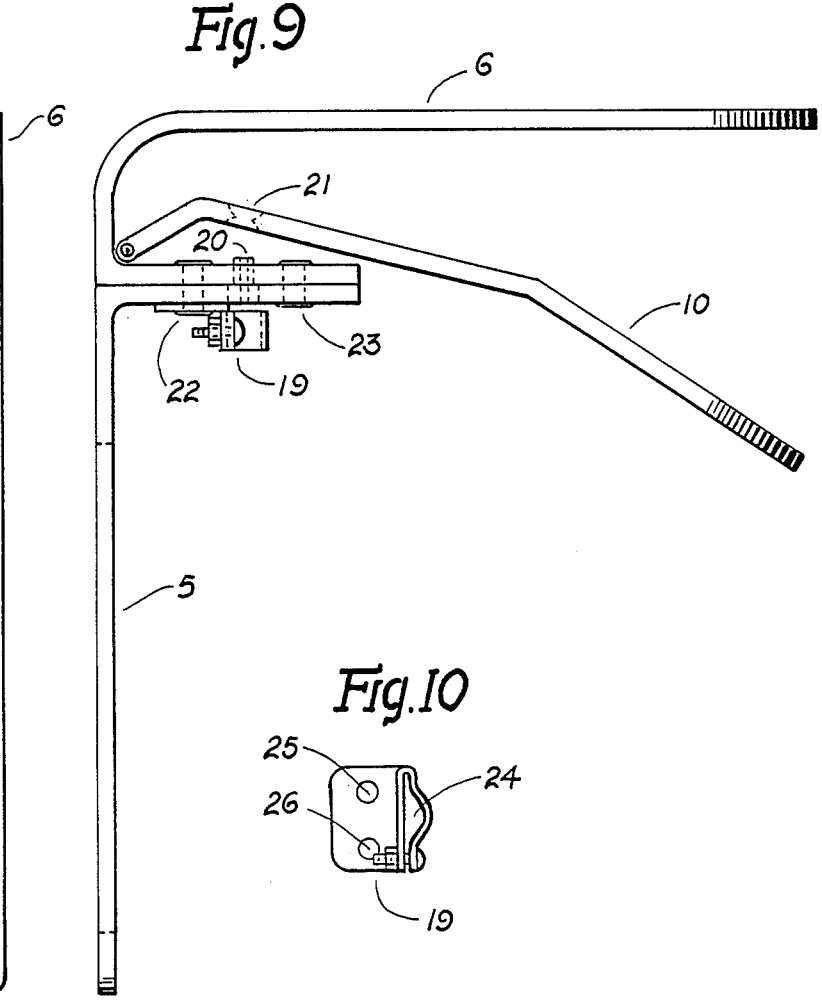
FIG. 9 shows a side view of the manipulator actuating/positioning system.
Figure 10:
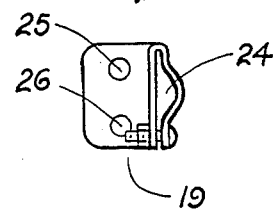
FIG. 10 shows a bottom view of clamp 19.

Slide track 15 is attached with a flathead machine screw at countersunk hole 16 and a stud and slotted nut that will be flush when tightened into the countersunk hole 17 with the threaded stud extending far enough to accommodate wing nut 4 which holds the manipulator actuating/positioning system FIGS. 8 and 9 with the threaded stud protruding through slot 18 which allows for adjustability.

The manipulator actuating/positioning system FIGS. 8 and 9 is comprised of slide 5, handle 6, lever 10 and clamp 19. Slide 5, handle 6 and clamp 19 can be assembled with rivets or appropriate fasteners at positions 22 and 23. Holes 25 and 26 in clamp 19 align with holes in slide 5 and handle 6 at position 22. The combination of slide 5, handle 6 and clamp 19 could also be formed as a unit. Lever 10 is attached by a hinge or other suitable means to allow pivoting at the end nearest handle 6. Hole 21, countersunk at top and bottom, should align with a line formed by opening 24 in clamp 19 and the holes in position 20 drilled large enough in slide 5 to accommodate the proximal end of the manipulator FIG. 11 but smaller in handle 6 to restrict the movement of the spring 27 and the proximal end of the manipulator FIG. 11 with a Teflon tube inserted in the hole in position 20 in handle 6 that will provide a smooth bearing surface for braided wire 28. Slot 18 should be long enough to allow adjustment to accommodate the full range of tube lengths the device is constructed to accommodate.

The manipulator FIG. 11 is comprised of a soft, flexible tube 2 surrounding a flat spring 27 of appropriate width and thickness to properly fit the nasally placed airway tubes the device is constructed to accommodate with said spring having a thickness adequate to prevent inappropriate distortion yet allowing adequate flexibility of the airway tubes it is constructed to accommodate and appropriate buckle/ripple if resistance is met in the patient's airway thus preventing trauma. A braided wire 28 is included inside the soft, flexible tube 2 lubricated with silicon and attached to the distal end of spring 27. Tip 1 can be formed of florescent red powdered acrylic mixed with solvent then flowed far enough into tube 2 to cover the distal point of attachment between spring 27 and braided wire 28. Tip 1 can be formed into a round, smooth tip after the acrylic sets up. The proximal end of spring 27 should have the temper drawn and be bent over the end of tube 2 to provide a smooth bearing surface for braided wire 28. The loop formed by bending spring 27 over the end of tube 2 will also help prevent the manipulator FIG. 11 from moving from its clamped position.

The manipulator FIG. 11 is assembled into the manipulator actuating/positioning system FIG. 9 by inserting braided wire 28 through opening 24 in clamp 19 and through the holes in slide 5 and the hole in the Teflon tube at position 20. Then braided wire 28 is passed through the countersunk hole 21 in lever 10. Soft tube 2 along with spring 27 are advanced with braided wire 28 through opening 24 in clamp 19 into the hole at position 20 in slide 5 and clamp 19 is tightened. A round brass ball drilled through the center is soldered to braided wire 28 just above lever 10 or some other suitable device attached to braided wire 28 which won't move along braided wire 28 once attached. A variation of construction could also allow the manipulator FIG. 11 to be snapped into the manipulator actuating/positioning system FIG. 9 making it more easily serviced or disposable.

The manipulator FIG. 11 is inserted through hole 11 and protrudes out the hole in fitting 3.

Slot 18 is placed over the stud protruding from slide track 15 at hole 17. Slide 5 is rested in slide track 15 and wing nut 4 is threaded onto the protruding stud protruding from slide track 15 hole 17 and made snug. Wing nut 4 is loosened and slide 5 is moved up or down in slide track 15 to adjust the position of the manipulator FIG. 11.

In operation, the distal end beginning with tip 1 of the manipulator FIG. 11 is inserted through the endotracheal tube adapter then through the endotracheal tube and the adapter inserted into fitting 3. Wing nut 4 is loosened and the device adjusted to position tip 1 just inside the distal end of the endotracheal tube and wing nut 4 is re-tightened.

After visualizing both nasal passages with a nasal speculum, applying a vasoconstrictor, lubricating the outside of the endotracheal tube and inserting a quantity of lubricant into the patient's nostril selected for tube passage, the tip of the endotracheal tube is inserted into the nostril. Lever 10 is squeezed together with handle 6 causing the proximal end of braided wire 28 to be drawn up toward handle 6 and providing potential flexion as illustrated in FIG. 11.

The endotracheal tube is advanced over the hard palate and soft palate and will curve over the soft palate into the posterior nasal pharynx then oral pharynx. At this point it would probably be best to discontinue squeezing lever 10 and handle 6 to avoid stimulating a gag reflex.

While listening through a stethoscope headset attached to port 7 and while advancing the endotracheal tube, rotate the device gently, gradually squeezing and/or releasing lever 10 and handle 6 until the loudest breath sounds are heared near the patient's glottic opening.

Advance the endotracheal tube through the patient's vocal cords into the patient's trachea as the patient breathes in.

Movement of one-way valve 13 on inspiration, movement of one-way valve 14 on expiration, fogging of tube 9 on expiration and continued loud breath sounds in the stethoscope headset attached to port 7 will confirm proper final placement of the endotracheal tube in the patient's airway.

The nasal intubation adjunct is removed by holding the adapter on the endotracheal tube with one hand and with a turning/pulling motion removing the nasal intubation adjunct with the other hand.

As per standard operating procedures, breath sounds over both right and left fields should be auscultated to confirm proper placement of the endotracheal tube. If breath sounds indicate one or the other main stem bronchi, usually the right, has been entered, withdraw the tube slightly until the problem is corrected.

The endotracheal tube cuff is inflated, the tube is secured in place and the procedure is complete.

While the above description contains many specificities, these should not be construed as limitations on the scope of the invention, but rather as an exemplification of one preferred embodiment thereof. Many other variations are possible, for example, an audible tone generated in the nasal intubation adjunct, a bright light at the distal end of the manipulator with batteries contained in the body of the unit, an attachment for nasal pharyngeal airways, electronic amplification of sounds heard through the nasal intubation adjunct, a disposable section, a variety of materials and methods of fabrication. Accordingly, the scope of the invention should be determined not by the embodiment illustrated, but by the appended claims and their legal equivalents.

I claim:

1. An instrument for allowing an operator to insert a nasally placed airway tube into a patient, said instrument comprising:
   a body having a first opening extending therethrough and a second opening extending into said body to connect to said first opening;
   tube attachment means for attaching the airway tube to said body and for allowing the airway tube to cooperate with said first opening in said body;
   manipulator means for flexing the airway tube, said manipulator means being insertable into said body and the airway tube through said first opening; and
   means attached to said second opening for detecting breathing sounds,
   means for attaching said manipulator to said body, said means for attaching the manipulator including a slide mounted to said manipulator;
   a slide track located on said body parallel to said first opening; and
   means for attaching said slide to said slide track; whereby said manipulator may be adjusted to a plurality of positions to accommodate a plurality of airway tube lengths.

2. The instrument of claim 1 wherein said tube attachment means further comprises:
   a first one way valve connected to allow air to be exhaled by the patient through the airway tube; and
   a second one way valve connected to allow air to be inhaled by the patient through the airway tube.

3. The instrument of claim 2 wherein said first one way valve is mounted to direct exhaled air in a direction substantially perpendicular to said first opening.

4. The instrument of claim 2 wherein said second one way valve is mounted to receive air in a direction substantially perpendicular to said first opening.

5. The instrument of claim 1 wherein said manipulator means further comprises:
   adjustable projection means extending into the airway tube for flexing the airway tube; and
   handle means for allowing the operator of said instrument to control said adjustable projection means.

6. The instrument of claim 5 wherein said adjustable projection means further comprises:
   a soft tube having a top opening at one end thereof, a closed tip at an other end thereof, and a hollow center extending from said top opening to said tip;
   a spring extending from said top opening toward said tip and having a distal end located substantially at said tip;
   constricting means for pulling said distal end of said spring toward said top opening, said constricting means being attached to said spring at said distal end, and extending through said soft tube to said top opening to attach to said handle means;
   whereby said adjustable projection means is flexed by adjusting said handle.

7. The instrument of claim 6 wherein said constricting means comprises a cable.

8. The instrument of claim 1 wherein said means for detecting breathing sounds comprises a stethoscope.

9. An instrument for allowing an operator to insert a nasally placed airway tube into a patient, said instrument comprising:
   a body having a first opening extending therethrough and a second opening extending into said body to connect to said first opening;
   tube attachment means for attaching the airway tube to said body and for allowing the airway tube to cooperate with said first opening in said body comprising
      a connecting fitting for receiving the airway tube, said fitting having a central opening for cooperating with said first opening,
      a first one way valve connected to said central opening for allowing air exhaled by the patient through the airway tube to exit said instrument in a direction away from said first opening, and
      a second one way valve connected to said central opening for allowing air inhaled by the patient through the airway tube to enter said instrument;
   manipulator means for flexing the airway tube, said manipulator means being insertable into said body and the airway tube through said first opening; said manipulator means further comprises an
   adjustable projection means extending into the airway tube for
      flexing the airway tube; and handle means for allowing the operator of said instrument to control said adjustable projection means,
   the adjustable projection means further comprises
      a soft tube having a top opening at one end thereof, a closed
      tip at an other end thereof, and a hollow center extending from said top opening toward said tip;
      a spring extending from said top opening toward said tip and
      having a distal end located substantially at said tip;
      constricting means for pulling said distal end of said spring
      toward said top opening, said constricting means being
      attached to said spring at said distal end, and extending
      through said soft tube and said top opening to attach to
      said handle means; whereby said adjustable projection means is flexed by
      adjusting said handle; and
   means attached to said second opening for detecting breathing sounds.

10. The instrument of claim 9 wherein said constricting means comprises a cable.

11. The instrument of claim 9 wherein said means for detecting breathing sounds comprises a stethoscope.

12. The instrument of claim 9 wherein said second opening is connected to said central opening.

13. An instrument for allowing an operator to insert a nasally placed airway tube into a patient, said instrument comprising:
   a body having a first opening extending therethrough;
   tube attachment means for attaching the airway tube to said body and for allowing the airway tube to cooperate with said first opening in said body comprising
  a connecting fitting for receiving the airway tube, said fitting having a central opening for cooperating with said first opening,
  a first one way valve connected to said central opening for allowing air exhaled by the patient through the airway tube to exit said instrument in a direction away from said first opening, and
  a second one way valve connected to said central opening for allowing air inhaled by the patient through the airway tube to enter said instrument;
manipulator means for flexing the airway tube, said manipulator means being insertable into said body and the airway tube through said first opening, said manipulator means comprising
  handle means for allowing the operator of said instrument to control said manipulator means, said handle means being slidably attached to said body,
  adjustable projection means extending into the airway tube for flexing the airway tube comprising
    a soft tube having a top opening at one end thereof, a closed tip at an other end thereof, and a hollow center extending from said top opening to said tip, said soft tube being attached to said handle
    a spring having a first end attached to said top opening and having a distal end located substantially at said tip,
    cable means for pulling said distal end of said spring toward said top opening, said cable means being attached to said spring at said distal end, and extending through said soft tube and said top opening to attach to said handle means; and
stethoscope means attached to said central opening for detecting breathing sounds.

* * * * *